United States Patent [19]

Arai et al.

[11] Patent Number: 4,577,025

[45] Date of Patent: Mar. 18, 1986

[54] METHOD OF PREPARING α-AROMATIC PROPIONIC ACIDS AND INTERMEDIATES THEREOF

[75] Inventors: Kazutaka Arai; Yoshio Ohara; Yashio Takakuwa; Toyoko Iizumi, all of Funabashi, Japan

[73] Assignee: Nissan Chemical Industries, Ltd., Tokyo, Japan

[21] Appl. No.: 527,179

[22] Filed: Aug. 26, 1983

Related U.S. Application Data

[63] Continuation of Ser. No. 332,961, Dec. 21, 1981.

[51] Int. Cl.$^4$ ............... C07D 211/34; C07D 333/02; C07D 333/24; C07D 277/60
[52] U.S. Cl. ............... 546/198; 568/328; 549/79; 548/494; 548/170; 548/572; 562/490; 562/465; 562/433; 562/427; 562/462; 562/496; 560/9; 560/152; 546/238
[58] Field of Search ............... 546/184, 198, 238; 568/31, 492, 493; 549/29, 79; 548/152, 494, 539, 170, 572; 562/490, 494, 465, 433, 427; 560/9, 15, 152

[56] References Cited

U.S. PATENT DOCUMENTS 2,642,429 6/1953 Clinton et al. ............... 546/184

Primary Examiner—Henry R. Jiles
Assistant Examiner—Robert C. Whittenbaugh
Attorney, Agent, or Firm—Frishauf, Holtz, Goodman & Woodward

[57] ABSTRACT

A method for the preparation of an ester of α-thio-α-aromatic propionic acid derivatives of the formula:

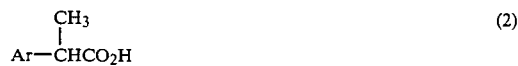

wherein $R^1$ is alkyl, phenyl or benzothiazolyl, $R^2$ is alkyl and Ar is an aromatic substituent.

The method comprises reacting an ester of α-chloro-α-thiopropionic acid of the formula:

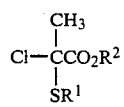

with an aromatic compound of the formula ARH, in the presence of a Lewis acid. The method provides good reactivity and positional selectivity in the Friedel-Crafts reaction. Many esters of the formula (2) are useful as pharmaceuticals, agricultural chemicals, perfumes or their intermediates.

26 Claims, No Drawings

METHOD OF PREPARING α-AROMATIC PROPIONIC ACIDS AND INTERMEDIATES THEREOF

This is a continuation of application Ser. No. 332,961, filed Dec. 21, 1981.

This is a continuation of application Ser. No. 332,961, filed Dec. 21, 1981.

The present invention relates to a novel method for preparing an ester of α-thio-α-aromatic propionic acide derivatives represented by the general formula (1):

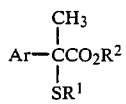

wherein $R^1$ is an alkyl group, a phenyl group or a benzothiazolyl group, $R^2$ is an alkyl group, and Ar is an armoatic substituent.

Many α-aromatic propionic acids represented by the general formula (2):

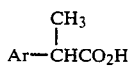

wherein Ar is an aromatic substituent, and which are obtainable by subjecting the compound of the general formula (1) to reductive desulfuration and hydrolysis, are useful as pharmaceuticals, agricultural chemicals, perfumes or their intermediates.

For instance, a series of compounds generally classified as profen type compounds have the above general formula (2) and exhibit remarkable antiinflammatory analgesic and antipyretic activities. A typical example is a compound called Naproxen, where Ar in the above formula (2) is 6-methoxy-naphtho-2-yl, which is widely used as a pharmaceutical.

Conventional methods for the preparation of Naproxen are generally classified into the following three categories.

(1) Methods in which 2-acetyl-6-methoxynaphthalene, as the starting material, is subjected to a carbon-introducing reaction. As the carbon-introducing reagent, an ylide compound and a cyano-forming reagent are used (Japanese Patent Publication No. 20545/73); a Witting reagent is used (Japanese Patent Publication No. 31868/77); potassium prussiate and ammonium carbonate are used (Japanese Laid-Open Patent Application No. 7215/72); methyl iodide is used after a Willgerodt reaction (Japanese Patent Publication No. 702/73) and the like.

(2) Methods in which 2-ethylcarbonyl-6-methoxynaphthalene, as the starting material, is subjected to a rearrangement reaction. As a reagent to facilitate the rearrangement, thallium (III) nitrate is used (Japanese Laid-Open Patent Application Nos. 4051/75, 23249/76, and 48648/74); p-toluene sulfonyl azide is used (Japanese Laid-Open Patent Application No. 15354/78); diphenyl phosphoric acid azide (DPPA) is used (Japanese Laid-Open Patent Application No. 59238/78) and the like.

(3) Methods in which a Friedel-Crafts reaction is used in the treatment of 2-methoxynaphthalene and α-(p-toluene sulfonyloxy) propionic acid in the presence of aluminum chloride (Japanese Laid-Open Patent Application No. 79258/74), and the like.

Among the above-mentioned methods, those belonging to category (1) may be regarded as the best as industrial methods since the reagents used therein are relatively inexpensive and they provide good yields. However, when the starting material 2-acetyl-6-methoxynaphthalene is prepared by the reaction of from 2-methoxynaphthalene with acethyl chloride, the Friedel-Grafts reaction used therefor, provides poor positional selectivity and tends to produce 1-acetyl-2-methoxynaphthalene (A) and 1-acetyl-7-methoxynaphthalene (B) as by-products, as identified by the following chemical structures:

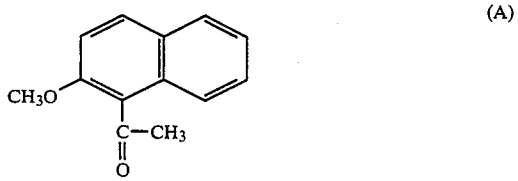

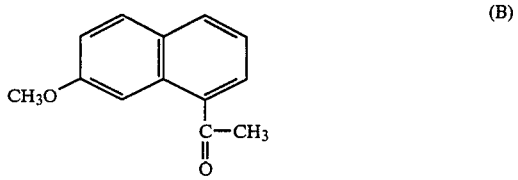

Even when it is attempted to improve the positional selectively with use of nitrobenzene as the solvent, the yield is still as low as 43% (see J. Chem, Soc. 181, (1966)), and this poor positional selectivity is a serious drawback.

The methods of category (2) have disadvantages that the starting material is not readily available for the same reason as in the case of the methods of category (1), and that the thallium salt having a strong toxicity or expensive reagents are used in those methods.

The methods of category (3) may be regarded as good ones since large building blocks are linked to each other in one step. However, they have drawbacks that they provided poor positional selectivity and worse reactivity than that of the methods of category (1) and that the yields are extremely poor.

It is seen that in each of the above cases, the Friedel-Grafts reaction of 2-methoxynaphthalene involved, constitutes a bottle neck. If the Friedel-Crafts reaction could be improved, the methods of category (3) would be more advantageous than the other methods since they involve a smaller number of process steps.

For many years, the present inventors have continued fundamental studies on the Friedel-Crafts reaction with respect to α-chlorosulfide, see (a) Tetrahedron Lett., 2183 (1975) and (b) Bull. Chem. Soc. Japan, 48, page 3319 (1975). In recent years, they have devoted themselves in the study of the application of this reaction to the synthesis of profen type compounds. As the result, they have succeeded in establishing a superior method in which the Friedel-Crafts reaction of α-chlorosulfide is used for the preparation of profene type compounds, particularly Naproxen.

There are two noteworthy features of the Friedel-Crafts reaction of α-chlorosulfide. Namely, if a halogenated alkyl with its α-position substituted by a sulfur atom (such as α-chlorosulfide) is used, firstly the reactivity is increased to permit the reaction to proceed under relatively moderate conditions, and secondly, the selectivity is improved, when the halogenated alkyl is treated with an aromatic compound in the Friedel-Crafts reaction condition in the presence of a Lewis acid.

Whereas, should the α-aromatic propionic acid derivative of the above general formula (2), which has now become readily available as the result of the present invention, be prepared by a Friedel-Crafts reaction of an ester of α-halopropionic acid having no sulfur substituent at its α-position and represented by the general formula (3):

$$X-\overset{CH_3}{\underset{|}{C}}HCO_2R^2 \qquad (3)$$

wherein X is a halogen atom and $R^2$ is an alkyl group, with an aromatic compound represented by the general formula (4):

$$ArH \qquad (4)$$

wherein Ar is an aromatic substituent, the reaction will have to be carried out at a high temperature and will take a long period of time, and the compound represented by the above general formula (3) undergoes a dehydrohalogenation reaction whereby it will be decomposed into an ester of acrylic acid represented by the general formula:

$$\overset{CH}{\underset{\|}{C}}HCO_2R^2$$

wherein $R^2$ is as defined above.

Consequently, the desired ester of α-aromatic propionic derivative acid is obtainable only in a small amount or not at all.

The present inventors have solved this serious problem by a novel method in which an ester of α-chloro-α-thiopropionic acid with its α-position substituted by a sulfur atom and having the general formula (5):

$$Cl-\overset{CH_3}{\underset{\underset{SR^1}{|}}{C}}CO_2R^2 \qquad (5)$$

wherein $R^1$ is an alkyl group, a phenyl group, or a benzothiazolyl group, and $R^2$ is an alkyl group, is used, and thereby improving the reactivity.

As mentioned above, a compound of the general formula (2) where Ar is 6-methoxy-naphth-2-yl, is called Naproxen. On the basis of the knowledge gained from the years of studies, the present inventors have found that both of the following two problems involved in the synthesis of Naproxen, i.e. (a) the reactivity of 2-methoxynaphthalene in the Friedel-Crafts reaction and (b) the positional selectivity, can be solved by using α-chlorosulfide as one of the reactants, and thus established a novel method wherein the ester of α-chloro-α-thiopropionic acid of the above structural formula (5) is used.

Namely, by carrying out the Friedel-Crafts reaction of an ester of α-chloro-α-thiopropionic acid of the above structural formula (5) with 2-methoxynaphthalene in the presence of a Lewis acid such as stannic chloride, it is possible to remarkably improve the reactivity as well as the positional selectivity over the reaction of an ester of α-halopropionic acid of the above structural formula (3) having no thio group with 2-methoxynaphthalene (see Comparative Examples) and to obtain the desired ester of α-thio-α-(6-methoxynaphth-2-yl) propionic acid (i.e. the compound of the general formula (1) where Ar is 6-methoxy-naphth-2-yl) in good yield. The product can then be subjected to reductive desulfuration with use of e.g. a Raney nickel, followed by hydrolysis to obtain Naproxen as the final product.

The process steps of this novel method are represented as follows:

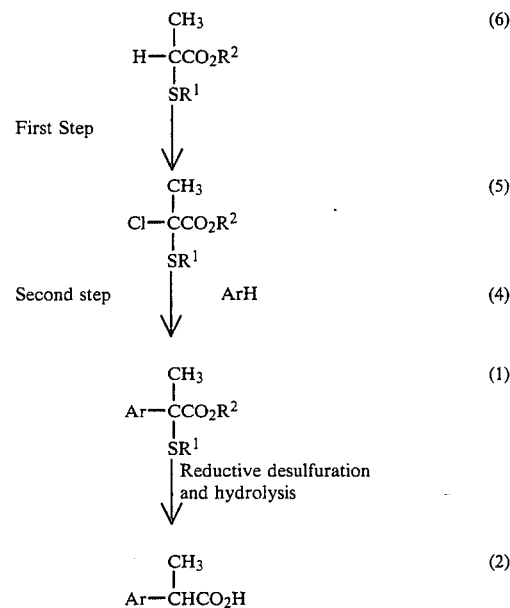

The reaction conditions of each step will be described below in detail:

The above first step is a step of treating an ester of α-thiopropionic acid of the general formula (6), wherein $R^1$ is an alkyl group, a phenyl group or a benzothiazolyl group and $R^2$ is an alkyl group, with a chlorinating reagent to form an ester of α-chloro-α-thiopropionic acid of the general formula (5) where $R^1$ and $R^2$ are as defined above.

The chlorinating reagent which may be used, includes N-chlorosuccinimide, sulfuryl chloride, chlorine, chlorinated isocyanuric acid, iodobenzene dichloride, and sulfenyl chloride. However, sulfuryl chloride and chlorine are preferred since they are readily available at low costs as industrial reagents. The chlorination reagent may be used in an amount of from 1 to 5 chemical equivalents. However, the amount is preferably from 1.05 to 1.5 chemical equivalents so that it is certainly reacted without substantial waste.

As the solvent, a non-polar solvent such as carbon tetrachloride, methylene chloride, chloroform, benzene or toluene, is preferably used. However, other solvents except for protic solvents and those having extremely strong polarity, may also be used. These solvents may be used also in combination, as the case requires.

The reaction can be conducted at a temperature of from −10 to 30° C. The higher the reaction temperature, the shorter the reaction time required. When the reaction is conducted at 20° C., for instance, it can be completed in from 10 minutes to 2 hours. Further, the reaction proceeds in extremely high yield, and in case the residual groups of the chlorination agent or the solvent does not interfere with the reaction of the subsequent step, the product may be used as formed. As an instance of such a case, there may be mentioned a case wherein carbon tetrachloride or methylene chloride is used as the solvent and sulfuryl chloride or chlorine is used as the chlorinating reagent.

In the case where the ester of α-chloro-α-thiopropionic acid of the general formula (5) is isolated by a process such as filtration, concentration under reduced pressure or distillation under reduced pressure, it is important that a base, water and any other nucleophilic reagents must be absent and the temperature should not be higher than 30° C., preferably not higher than 10° C.

The above-mentioned second step is a step of treating the ester of α-chloro-α-thiopropionic acid of the general formula (5) with the aromatic compound of the general formula (4) in the presence of a Lewis acid to prepare an ester of α-thio-α-aromatic propionic acid represented by the general formula (1).

As the aromatic compound to be used, there may be mentioned, for instance, those being highly electron-rich compounds such as ones represented by the general formula (4) where Ar is a 4-alkylphenyl group, a 4-phenylphenyl group, a 4-alkoxyphenyl group, a 4- and/or -2-hydroxyphenyl group, or a 4-disubstituted amino phenyl group; these phenyl groups further substituted by an electron donative alkyl, alkoxy, hydroxy or disubstituted amino group; and these phenyl groups further substituted by one electron attractive halogen substituent; or condensed-ring aromatic substituents such as a naphthyl group, a 6-methoxy-naphth-2-yl group, and a 2-methoxy-naphth-1-yl group; or hetero aromatic substituents such as a 2-thienyl group, a 3-indolyl group and an N-alkylpyrrolyl group.

As the Lewis acid to be used, there may be mentioned stannic chloride, titanium tetrachloride, zinc bromide, ferric chloride, aluminium chloride and zinc chloride etc. However, stannic chloride is particularly preferred as it gives high yield. The Lewis acid is used in an amount of from 0.05 to 5 chemical equivalents. However, an amount of from 0.8 to 2.0 chemical equivalents is preferred to carry out the reaction readily and efficiently.

As the solvent, there may be used a solvent which is not directly involved in the reaction, such as carbon tetrachloride, methylene chloride, carbon disulfide, nitromethane or nitrobenzene. They may be used also in combination as a solvent mixture, as the case requires.

The reaction can be conducted in a temperature range of from $-10$ to $50°$ C. The reaction is slow at a low temperature. Whereas, at a high temperature, it is likely that the ester of α-chloro-α-thiopropionic acid of the general formula (5) undergoes a dehydrochlorination reaction to give an ester of α-thioacrylic acid. For these reasons, a temperature of from 0 to 35° C. is preferred. Under this temperature condition, the reaction is sufficiently completed within 4 hours.

As the method for the reductive desulfuration after the completion of the second step, there may be mentioned, for instance, a method in which activated nickel such as a Raney nickel is used; a method in which nascent hydrogen generated by e.g. zinc-acetic acid or sodium-t-butyl alcohol, is used; a method in which a reducing agent having an affinity with sulfur, such as sodium methylmercaptide; or a method in which the product of the second step is heated directly, or heated after converted to a sulfoxide by oxidation, to produce an ester of acrylic acid, followed by hydrogenation. As the reagent for use in the hydrolysis, there may be mentioned, for instance, an aqueous solution or a water-alcohol solution of sodium hydroxide, potassium hydroxide or barium hydroxide.

Now, the invention will be described in detail with reference to Examples, Comparative Examples and Reference Examples.

EXAMPLE 1

Preparation of ethyl α-(ethylthio)-α-(6-methoxynaphth-2-yl) propionate

Dissolved in 20 ml of methylene chloride were 1.87 g (one chemical equivalent) of ethyl α-chloro-α-(ethylthio) propionate and 1.50 g (one chemical equivalent) of 2-methoxynaphthalene. To the solution thereby obtained, 2.65 g (1.1 chemical equivalents) of stannic chloride was added at a temperature of from 20 to 25° C., and stirred for one hour. Then, 20 g of water was added thereto in an ice-cold bath, followed by phase separation. The organic layer was washed with 10 g of water, and then concentrated under reduced pressure, whereby 3.20 g of yellowish oily substance was obtained. A portion of the substance was subjected to thin layer chromatography thereby to obtain test samples for analyses and at the same time the purity was thereby confirmed to be at least 65%. From its NMR, IR, MS, etc. this substance was found to be ethyl α-(ethylthio)-α-(6-methoxynaphth-2-yl) propionate, which was colourless oily substance.

NMR (CDCl$_3$):δ1.12 (3H, t, 7 Hz), 1.24 (3H, t, 7 Hz), 1.86 (3H, s), 2.50 (2H, dq, 3 Hz and 7 Hz), 3.86 (3H, s), 4.23 (2H, q, 7 Hz), 6.9~7.9 (6H, m).

IR (neat): 2950, 1715, 1600, 1382, 1260, 1180, 1030, 852 cm$^{-1}$.

MS (m/e): M$^+$=318.1223 (calculated value: C$_{18}$H$_{22}$O$_3$S=318.1228), 318 (30), 258 (23), 257 (100), 245 (26), 183 (50).

EXAMPLE 2

Preparation of ethyl α-(methylthio)-α-(6-methoxynaphth-2-yl) propionate

In 8.0 g of carbon tetrachloride, 1.48 g (1.05 chemical equivalents) of ethyl α-(methylthio) propionate was dissolved, and 1.48 g (1.16 chemical equivalents) of N-chlorosuccinimide was added thereto in separate portions while maintaining the solution at a temperature of from 18 to 22° C. Stirring was continued for further one hour and 30 minutes at the same temperature. The reaction solution was promptly filtered, and washed with 6.0 g of carbon tetrachloride, whereby the succinimide floating in a form of crystals was filtered off. The carbon tetrachloride solution of ethyl α-chloro-α-(methylthio) propionate thus obtained was dropwise added to a solution which was prepared by firstly dissolving 1.50 g (one chemical equivalent) of 2-methoxynaphthalene in 25 g of methylene chloride and then adding 2.65 g (1.07 chemical equivalents) of stannic chloride, while maintaining the temperature at from 25 to 30° C. During the latter half of the dropwise addition, formation of bubbles was observed which were presumably bubbles of hydrogenchloride.

After the completion of the dropwise addition, stirring was continued for further 45 minutes at the same temperature. Then, 10 ml of water was added, and phase separation was conducted. The organic layer was washed with water three times and then concentrated under reduced pressure, whereupon 2.75 g of yellowish oily substance was obtained. From its NMR, the substance was found to be composed mainly of ethyl α-(methylthio)-α-(6-methoxynaphth-2-yl) propionate. A portion of this oily substance was subjected to thin layer chromatography separation, whereby test samples for analyses were obtained and at the same time, the yield was confirmed to be at least 72%.

Boiling point: 164 to 168° C./0.25 mmHg.

NMR (CDCl$_3$): δ1.27 (3H, t, 7 Hz), 1.88 (3H, s), 1.97 (3H, s), 3.89 (3H, s). 4.27 (2H, q, 7 Hz), 7.05∼7.95 (6H, m).

IR (neat): 2950, 1712, 1620, 1595, 1380, 1230, 1177, 1100, 1027, 850 cm$^{-1}$.

MS (m/e): M$^+$=304.1151 (calculated value: C$_{17}$H$_{20}$O$_3$S=304.1133), 304 (13), 258 (14), 257 (54), 256 (40), 211 (12), 184 (15), 183 (100).

COMPARATIVE EXAMPLE 1

Reaction of ethyl α-bromopropionate with 2-methoxynaphthalene

Under the same conditions as in Example 2, 1.45 g of 2-methoxynaphthalene and 1.81 g of ethyl α-bromopropionate were dissolved in 10 g of methylene chloride and 6 g of carbon tetrachloride, and 2.6 g of stannic chloride was further added. The mixture was stirred at 20° C. for 26 hours. However, no Friedel-Crafts reaction product was obtained. The mixture was refluxed under heating for further 5 hours, and yet no reaction occurred.

EXAMPLE 3

Preparation of ethyl α-(methylthio)-α-(6-methoxynaphth-2-yl) propionate

In 10 g of carbon tetrachloride, 1.48 g of ethyl α-(methylthio) propionate was dissolved, and 1.48 g of sulfury chloride was dropwise added at 10° C., and the solution was stirred for 40 minutes. This reaction solution was added to a solution prepared by dissolving 1.21 g of 2-methoxynaphthalene in 13 g of methylene chloride, at 5° C., and 2.7 g of stannic chloride was further added at a temperature of from 5 to 10° C. The solution was stirred for 40 minutes. Then, 15 g of water was added thereto and phase separation was conducted twice each time with 10 g of water. The organic layer was concentrated under reduced pressure, whereupon 2.53 g of yellowish substance was obtained. As a result of the analysis by gas chromatography, it was found that ethyl α-(methylthio)-α-(6-methoxynaphth-2-yl) propionate was obtained in 62% yield. The analytical values were identical to those obtained in Example 2.

EXAMPLE 4

Preparation of ethyl α-(methylthio)-α-(6-methoxynaphth-2-yl) propionate

A carbon tetrachloride solution of ethyl α-chloro-α-(methylthio) propionate prepared in a manner similar to Example 2 (the solution containing 1.48 g of ethyl α-(methylthio) propionate), was added to a solution prepared by dissolving 0.76 g of 2-methoxynaphthalene in 11 g of nitromethane, at a temperature of from 20 to 25° C., and 1.4 ml of titanium tetrachloride was further added. The solution was stirred at the same temperature for 3 hours. The reaction solution was washed twice with water, and concentrated under reduced pressure, whereupon 1.76 g of orange coloured oily substance was obtained. As a result of the analysis by gas chromatography, it was found that ethyl α-(methylthio)-α-(6-methoxynaphth-2-yl) propionate was obtained in 25% yield. The analytical values were identical to those obtained in Example 2.

EXAMPLE 5

Preparation of α-(ethylthio)-α-(3-chloro-4-piperidinophenyl) propionic acid in which ArH was 1-chloro-4-piperidinobenzene A carbon tetrachloride solution of ethyl α-chloro-α(ethylthio) propionate prepared in a manner similar to Example 2 (the reaction of 1.64 g of ethyl α-(ethylthio) propionate with 1.47 g of N-chlorosuccinimide), was dropwise added at 30° C. to a solution prepared by dissolving 1.62 g of 1-chloro-2-piperidinobenzene and 2.6 g of stannic chloride in 20 g of methylene chloride, and the mixture was stirred for 3 hours. Then, 60 ml of water was added for phase separation, and the organic layer was washed with 60 ml of a 10% hydrochloric acid aqueous solution. To the water layer, about 42 g of a 50% sodium hydroxide aqueous solution was added to bring the pH to 11, and extraction was conducted with toluene. After washing with water, the solution was concentrated under reduced pressure, whereupon yellow oily substance containing 2.4 g of ethyl α-(ethylthio)-α-(3-chloro-4-piperidinophenyl) propionate was obtained. The substance was subjected to hydrolysis and the acidic component was extracted with an aqueous alkaline solution, then adjusted to a pH of about 5 with an aqueous hydrochloric acid solution, and subjected to toluene extraction. The extracted product was concentrated under reduced pressure, whereupon 0.13 g of yellowish oily substance was obtained. From its NMR and GC-MS after the treatment with diazomethane, the substance was found to be α-(ethylthio)-α-(3-chloro-4-piperidinophenyl) propionic acid.

NMR (CDCl$_3$): δ1.25 (3H, t, 7 Hz), 1.55∼1.8 (6H, m), 2.85∼3.1 (4H, m), 2.35 (2H, q, 7 Hz), 6.9∼7.5 (3H, m).

MS (m/e): 343 (4), 341 (13, M$^+$), 283 (6), 282 (36), 281 (18), 280 (100), 220 (4).

EXAMPLE 6

Preparation of ethyl α-(ethylthio)-α-(4-methoxyphenyl) propionate in which ArH was anisole To a carbon tetrachloride solution of ethyl α-chloro-α-(ethylthio) propionate prepared in a manner similar to Example 2 (the reaction of 0.16 g of ethyl α-(ethylthio) propionate with 0.14 g of N-chlorosuccinimide), 10 g of methylene chloride and 1.0 g of anisole were added, and then 0.3 g of stannic chloride was added at 20° C. The mixture was stirred for 1.5 hours. Then, water and toluene were added thereto and phase separation was conducted. The organic layer was washed with water and concentrated under reduced pressure. The yellowish oily substance thereby obtained was subjected to thin layer chromatography separation, whereupon 0.17 g of colourless oily substance was obtained. From its NMR, IR and MS, the substance was found to be ethyl α-(ethylthio)-α-(4-methoxyphenyl) propionate.

NMR (CDCl$_3$): δ1.13 (3H, t, 7 Hz), 1.25 (3H, t, 7 Hz), 1.78 (3H, s), 2.47 (2H, q, 7 Hz), 3.78 (3H, s), 4.22 (2H, q, 7 Hz), 6.87 (2H, d, 10 Hz), 7.40 (2H, d, 10 Hz).

IR (neat): 1718, 1602, 1505, 1250, 1185, 1100, 1035, 830 cm$^{-1}$.

MS (m/e): M$^+$=268.1121 (calculated value: C$_{14}$H$_{20}$O$_3$S=268.1131), 268 (13), 208 (19), 207 (100), 206 (29), 195 (28), 161 (10), 134 (16), 133 (68).

EXAMPLE 7

Preparation of ethyl α-(methylthio)-α-(4-methoxyphenyl) propionate in which ArH was anisole To a carbon tetrachloride solution of ethyl α-chloro-α-(methylthio) pripionate prepared in a manner similar to Example 3, 10 g of methylene chloride and 1.08 g of anisole were added, and then 2.6 g of stannic chloride was further added at 20° C. The mixture was stirred for 1.5 hours. After washing with water, toluene and water were added thereto and phase separation was conducted. The organic layer was further washed with water and concentrated under reduced pressure, whereupon 1.95 g of almost colourless oily substance was obtained. From its NMR and GC, the substance was found to be almost pure ethyl α-(methylthio)-α-(4-methoxyphenyl) propionate. The yield was about 77%. A portion of the substance was subjected to thin layer chromatography separation to obtain test samples for analyses.

NMR (CDCl$_3$): δ1.25 (3H, t, 7 Hz), 1.77 (3H, s), 1.97 (3H, s), 3.77 (3H, s), 4.23 (2H, q, 7 Hz), 6.86 (2H, d, 10 Hz), 7.40 (2H, d, 10 Hz).

IR (neat): 1715, 1600, 1505, 1245, 1185, 1180, 1030, 830 cm$^{-1}$.

MS (m/e): M$^+$=254.0977 (calculated value: C$_{13}$H$_{18}$O$_3$S=254.0976), 254 (11), 208 (15), 207 (100), 206 (30), 181 (29), 134 (16), 133 (67).

EXAMPLE 8

Preparation of ethyl α-(methylthio)-α-(2-thienyl) propionate in which ArH was thiophene A carbon tetrachloride solution of ethyl α-chloro-α-(methylthio) propionate prepared in a manner similar to Example 3, was added to 10.5 g of a methylene chloride solution containing 0.5 g of thiophene, and 2.6 g of stannic chloride was further added at a temperature of from 15 to 20° C. The mixture was stirred for one hour. The reaction solution was washed with 10 ml and 5 ml of water, and then concentrated under reduced pressure, whereupon 1.5 g of brown oily substance was obtained. A portion of the substance was subjected to thin layer chromatography separation, and yellowish oily substance thereby obtained was used as the test sample for analyses. From its NMR, etc., this substance was found to be ethyl α-(methylthio)α-(2-thienyl) propionate.

NMR (CDCl$_3$): δ1.30 (3H, t, 7 Hz), 1.92 (3H, s), 2.05 (3H, s), 4.23 (2H, q, 7 Hz), 6.75~7.35 (3H, m).

IR (neat): 1718, 1250, 1230, 1108, 702 cm$^{-1}$.

MS (m/e): M$^+$=230.0393 (calculated value: C$_{10}$H$_{14}$O$_2$S$_2$=230.0433), 230 (19), 185 (16), 184 (34), 183 (17), 159 (11), 157 (87), 137 (36), 109 (45).

EXAMPLE 9

Preparation of ethyl α-(methylthio)-α-(4-hydroxyphenyl) propionate in which ArH was phenol A carbon tetrachloride solution of ethyl α-chloroα-(methylthio) propionate prepared in a manner similar to Example 3 was added to a solution prepared by dissolving 1.0 g of phenol in 10 ml of methylene chloride, and 2.6 g of stannic chloride was further added at 20° C. The mixture was stirred for 3 hours. Water was added thereto and phase separation was conducted. Thereafter, water and toluene were added and phase separation was conducted. The organic solution was further washed with water and then concentrated under reduced pressure, whereupon 2.54 g of greenish oily substance was obtained. From its NMR, etc., this substance was found to be almost pure ethyl α-(methylthio)-α-(4-hydroxyphenyl) propionate. The substance was further purified by subjecting it to thin layer chromatography and used as the test sample for analyses, which was colourless oily substance.

NMR (CDCl$_3$): δ1.27 (3H, t, 7 Hz), 1.78 (3H, s), 4.24 (2H, q, 7 Hz), 6.2 (1H, broad, s), 6.80 (2H, d, 9 Hz), 7.34 (2H, d, 9 Hz).

IR (neat): 3270, 1715, 1690, 1605, 1505, 1240, 1100, 1015, 835 cm$^{-1}$.

MS (m/e): M$^+$=240.0798 (calculated value: C$_{12}$H$_{16}$O$_3$S=240.0818), 240 (26), 194 (23), 193 (100), 192 (24), 167 (80), 147 (16), 119 (44).

COMPARATIVE EXAMPLE 2

Reaction of ethyl α-bromopropionate with phenol

Under the same onditions as in Example 9, 0.94 g of phenol and 1.81 g of ethyl α-bromopropionate were dissolved in 10 g of methylene chloride and 6 g of carbon tetrachloride, and 2.6 g of stannic chloride was added. The mixture was stirred at 20° C. for 26 hours, a Friedel-Crafts reaction product (ethyl α-(4-hydroxyphenyl) propionate or ethyl α-(2-hydroxyphenyl) propionate) was not obtained. The mixture was refluxed under heating for further 5 hours, and yet no reaction occurred.

EXAMPLE 10

Preparation of ethyl α-(methylthio)-α-(4-isobutylphenyl) propionate in which ArH was isobutylbenzene A carbon tetrachloride solution of ethyl α-chloro-α-(methylthio) propionate prepared in a manner similar to Example 3, was added to a solution prepared by dissolving 1.5 g of isobutylbenzene in 8 g of methylene chloride, and 2.6 g of stannic chloride was further added. The mixture was stirred for one hour. Then, 20 ml of water was added and phase separation was conducted. Further, toluene and water were added and after insoluble matters were filtered off, phase separation was conducted. The organic layer was concentrated to obtain 0.60 g of yellowish oily substance. A portion thereof was purified by thin layer chromatography, whereby test samples for analyses of ethyl α-(methylthio)-α-(4-isobutylphenyl) propionate were obtained. The product was colourless oily substance.

NMR (CDCl$_3$): δ0.90 (6H, d, 7 Hz), 1.26 (3H, t, 7 Hz), 1.78 (3H, s), 1.98 (3H, s), 1.6~2.3 (1H, m), 2.45 (2H, d, 7 Hz), 4.24 (2H, q, 7 Hz), 7.13 (2H, d, 9 Hz), 7.37 (2H, d, 9 Hz).

IR (neat): 2920, 1715, 1230, 1100, 1018 cm$^{-1}$.

MS (m/e): M$^+$=280.1474 (calculated value: C$_{16}$H$_{24}$O$_2$S=280.1494), 280 (3), 234 (10), 233 (63), 208 (21), 207 (100), 205 (11).

EXAMPLE 11

Preparation of ethyl α-(methylthio)-α-(4-phenylphenyl) propionate in which ArH was biphenyl A carbon tetrachloride solution of ethyl α-chloro-α-(methylthio) propionate prepared in a manner similar to Example 3, was added to a solution prepared by dissolving 1.4 g of biphenyl in 10 g of methylene chloride, and 2.6 g of stannic chloride was further added at 20° C. The mixture was stirred for one hour. After the same treatment as in Example 10, the organic layer was concentrated to obtain 1.8 g of yellowish oily substance. A portion thereof was purified by thin layer chromatography, whereby test samples for analyses of ethyl α-(methylthio)-α-(4-phenylphenyl) propionate were obtained. The product was yellowish oily substance.

NMR (CDCl$_5$): δ1.29 (3H, t, 7 Hz), 1.83 (3H, s), 2.03 (3H, s), 4.27 (2H, q, 7 Hz), 7.2~7.8 (9H, m).

MS (m/e): 300 (16, M+), 254 (21), 253 (100), 227 (63), 53 (45).

REFERENCE EXAMPLE 1

Preparation of ethyl α-(6-methoxynaphth-2-yl) propionate

Dissolved in 6 ml of ethyl alcohol was 0.18 g of ethyl α-(methylthio)-α-(6-methoxynaphth-2-yl) propionate, and 20 ml of a Raney nickel suspension (which was prepared from NDHT-90 manufactured by Kawaken Fine Chemical Co. by solvent substitution with ethyl alcohol) was added. The mixture was stirred at 40° C. for 30 minutes, then filtered, and washed three times with toluene, once with water and once with toluene for complete washing. The filtered and washed solution was separated, and the toluene layer was concentrated under reduced pressure, whereupon 0.15 g of almost colourless oily substance was obtained. From its NMR, IR, MS, etc., this substance was found to be ethyl α-(6-methoxynaphth-2-yl) propionate. When left to stand still, it solidified. The yield was 95%.

Melting point: 50 to 52° C.

Boiling point: 149° C./0.2 mmHg.

NMR (CDCl$_3$): δ1.19 (3H, t, 7 Hz), 1.56 (3H, d, 7 Hz), 3.83 (1H, q, 7 Hz), 3.88 (3H, s), 4.12 (2H, q, 7 Hz), 6.9~7.8 (6H, m).

IR (KBr): 2955, 1722, 1600, 1183, 1160, 1030, 860, 823, 480 cm$^{-1}$.

MS (m/e): M=258.1291 (calculated value: C$_{16}$H$_{18}$O$_3$=258.1256), 258 (100), 186 (22), 185 (76).

REFERENCE EXAMPLE 2

Preparation of ethyl α-(6-methoxynaphth-2-yl) propionate

To 0.18 g of ethyl α-(methylthio)-α-(6-methoxynaphth-2-yl) propionate, 2.0 g of acetic acid, 0.14 g of zinc powder and 0.01 g of anhydrous copper sulfate were added, and the mixture was refluxed under heating for 2 hours. After the acetic acid was distilled off under reduced pressure, 5 g of water and 20 g of toluene were added thereto and phase separation was conducted. The toluene layer was further washed with water and then the toluene was distilled off under reduced pressure, whereupon 0.14 g of colourless oily substance was obtained. From its NMR, IR, MS, etc., this substance was found to be ethyl α-(6-methoxynaphth-2-yl) propionate. The yield was 90%. The analytical values were the same as those obtained by Reference Example 1.

REFERENCE EXAMPLE 3

Preparation of ethyl α-(6-methoxynaphth-2-yl) propionate

Dissolved in 4 ml of dimethylformamide was 0.18 g of ethyl α-(methylthio)-α-(6-methoxynaphth-2-yl) propionate, and the solution thereby obtained was dropwise added at room temperature to an ethylalcohol-dimethylformamide (1:1) solution of sodium methylmercaptide (the solution being prepared by adding 0.06 g of metal sodium to 4 ml of ethyl aochol, after the reaction, blowing in 0.20 g of methylmercaptane and further adding 4 ml of dimethylformamide). The mixture was stirred for one hour, and then heated to 60° C. and stirred for 30 minutes. After cooling the reaction solution, 8 g of water, 2.5 g of an aqueous hydrochloric acid solution, and 5 g of toluene were added and phase separation was conducted. The toluene layer was washed twice with water, and then concentrated under reduced pressure, whereupon 0.14 g of yellowish oily substance was obtained. From its NMR, IR, MS, etc., this substance was found to be ethyl α-(6-methoxynaphth-2-yl) propionate. The yield was 90%. The analytical values were the same as those obtained by Reference Example 1.

REFERENCE EXAMPLE 4

Preparation of ethyl α-(6-methoxynaphth-2-yl) propionate

Dissolved in 6 ml of acetic acid was 0.56 g of ethyl α-(methylthio)-α-(6-methoxynaphth-2-yl) propionate, and 6.9 ml of an acetic acid solution containing 1% of hydrogen peroxide (i.e. a solution prepared by adding 1 ml of a 30% hydrogen peroxide aqueous solution to 31 ml of acetic acid) was added thereto. The mixture was stirred at a temperature of from 7° to 12° C. for 3 hours and at a temperature of from 18° to 21° C. for 2 hours. Then, 20 ml of chloroform and 20 ml of water were added thereto and phase separation was conducted. Then, the organic layer was washed four times with water, each time with 20 ml of water, and after drying over anhydrous magnesium sulfate, concentrated under reduced pressure, and 0.71 g of yellowish oily substance was obtained. Then, the oily substance was distilled under reduced pressure and heating, whereupon 0.42 g of yellowish oily substance was obtained. From its NMR, IR, MS, etc., this substance was found to be ethyl α-(6-methoxynaphth-2-yl) acrylate. The yield was 88%.

Melting point: 59 to 62° C.

Boiling point: 152 to 175° C./0.1 to 0.15 mmHg.

NMR (CDCl$_3$): δ1.32 (3H, t, 7 Hz), 3.91 (3H, s), 4.33 (2H, q, 7 Hz), 6.00 (1H, s), 6.40 (1H, s), 7.0~8.0 (6H, m).

IR (neat): 1713, 1623, 1600, 1260, 1220, 1180, 1035 cm$^{-1}$.

MS (m/e): M+=256.1088 (calculated value: C$_{16}$H$_{16}$O$_3$=256.1098).

This compound was dissolved in 10 ml of ethyl alcohol, and 62 ml of a Raney nickel suspension (which was prepared from NDHT-90 manufactured by Kawaken Fine Chemical Co. by solvent substitution with ethyl alcohol) was added thereto. The mixture was stirred at room temperature under a hydrogen atmosphere for 3 hours and at 40° C. for one hour. The reaction mixture was subjected to decantation, the decantation residue was washed twice with 20 ml of toluene, and the toluene solutions thereby obtained were combined with the reaction solution. The solution thus obtained was then concentrated under reduced pressure. Then, 40 ml of toluene and 10 ml of water were added thereto and phase separation was conducted. The toluene layer was washed twice, each time with 10 ml of water, and then concentrated under reduced pressure, whereupon 0.365 g of colourless oily substance was obtained. When left to stand still, the substance solidified. From its NMR, IR, MS, etc., this substance was found to be ethyl α-(6-methoxynaphth-2-yl) propionate. The yield was 86%. The analytical values were the same as those obtained by Reference Example 1.

REFERENCE EXAMPLE 5

Preparation of α-(6-methoxynaphth-2-yl) propionic acid

Dissolved in 3.0 g of ethyl alcohol was 0.95 g of ethyl α(6-methoxynaphth-2-yl) propionate, and 1.0 g of water and 0.16 g of sodium hydroxide were added thereto. The mixture was refluxed under heating for 15 minutes. Then, 2 g of water and 5 g of toluene were added and phase separation was conducted. To the water layer thereby obtained, 15 g of toluene and 1.35 g of concentrated hydrochloric acid were added, and phase separation was conducted at 70° C. After washing with water, the organic layer was concentrated under reduced pressure, whereupon 0.80 g of almost colourless crystals were obtained. The yield was 95%. These crystals were recrystallized once from toluene to obtain a test sample for analyses.

The analytical values of this product was as indicated below, and corresponded pretty well to those of the standard sample of α-(6-methoxynaphth-2-yl) propionic acid.

Melting point: 156.8° to 157.3° C.

NMR (CDCl$_3$): δ1.57 (3H, d, 7 Hz), 3.83 (1H, q, 7 Hz), 3.86 (3H, s), 6.9~8.05 (6H, m), 8.0 (1H, broad, s).

IR (KBr): 2930, 1690, 1595, 1380, 1260, 1223, 1027, 920, 853, 820, 673, 480 cm$^{-1}$.

MR (m/e): 230 (93, M+), 185 (100).

We claim:

1. A method of preparing an ester of α-thio-α-aromatic propionic acid derivatives represented by the general formula:

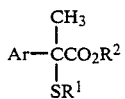

wherein R$^1$ is an alkyl group, a phenyl group or a benzothiazolyl group, R$^2$ is an alkyl group and Ar is an aromatic group, which comprises reacting an ester of α-chloro-α-thiopropionic acid represented by the general formula:

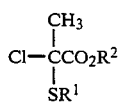

wherein R$^1$ and R$^2$ are as defined above, with an aromatic compound represented by the general formula:

ArH wherein Ar is as defined above, in the presence of a Lewis acid.

2. A method of preparing an α-aromatic propionic acid of the formula

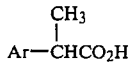

wherein Ar is an aromatic group, comprising
(a) reacting a compound of the formula

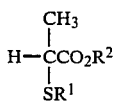

wherein R$^1$ is selected from the group consisting of an alkyl group, a phenyl group and a benzothiazolyl group, and R$^2$ is an alkyl group, with a chlorinating agent in the presence of a non-polar solvent to produce an α-chlorinated product;

(b) reacting said α-chlorinated product with a compound having the formula ArH, wherein Ar is selected from the group consisting of 4-alkylphenyl, 4-phenylphenyl, 4-alkoxyphenyl, 4-hydroxyphenyl, 2-hydroxyphenyl 2,4-dihydroxyphenyl, 4-disubstituted aminophenyl, and wherein each of said phenyl groups may be further substituted by a substituent selected from the group consisting of alkyl, alkoxy, hydroxy, disubstituted amino, halogen; naphthyl, 6-methoxynaphth-2-yl, 2methoxynaphth-1-yl, 2-thieny, 1,3-indolyl and N-alkylpyrrolyl, in the presence of a Lewis acid and a non-reactive solvent to produce a compound having the formula

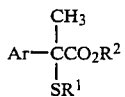

wherein Ar, R$^1$ and R$^2$ are as defined above;

(c) desulfurizing the product of step (b) to form a desulfurized product; and (d) hydrolyzing the desulfurized product in the presence of an aqueous solution or an aqueous alcohol solution.

3. The method of claim 2 wherein the reaction of step (a) is conducted at a temperature of from −10° C. to 30° C.

4. The method of claim 2 wherein the chlorinating agent is selected from the group consisting of N-chlorosuccinimide, sulfuryl chloride, chlorine, chlorinated isocyanuric acid, iodobenzene dichloride and sulfenyl chloride.

5. The method of claim 2 wherein the chlorinating agent is used in an amount of from 1 to 5 chemical equivalents.

6. The method of claim 6 wherein the non-polar solvent is selected from carbon tetrachloride, methylene chloride, chloroform, benzene and toluene.

7. The method of claim 2 wherein the chlorinating agent is selected from sulfuryl chloride and chlorine and the non-polar solvent is selected from carbon tetrachloride and methylene chloride.

8. The method of claim 2 wherein the Ar group is selected from 6-methoxy-naphth-2-yl, 4-methoxyphenyl and 4-hydroxyphenyl.

9. The method of claim 2 wherein the Lewis acid is selected from the group consisting of stannic chloride, titanium tetrachloride, zinc bromide, ferric chloride, aluminum chloride and zinc chloride.

10. The method of claim 9 wherein the Lewis acid is present in an amount of from 0.05 to 5.0 chemical equivalents.

11. The method of claim 2 wherein the non-reactive solvent is at least one solvent selected from the group consisting of carbon tetrachloride, methylene chloride, carbon disulfide, nitromethane and nitrobenzene.

12. The method of claim 2 wherein the step of reacting said α-chlorinated product with a compound having the formula ArH is conducted at a temperature between −10° C. and 50° C.

13. The method of claim 2 further comprising desulfurizing the product of step (b) in the presence of activated nickel.

14. The method of claim 2 further comprising desulfurizing the product of step (b) in the presence of (a) zinc and acetic acid or (b) sodium-t-butyl alcohol.

15. The method of claim 2 further comprising desulfurizing the product of step (b) in the presence of a reducing agent having an affinity for sulfur.

16. The method of claim 15 wherein the reducing agent is sodium methylmercaptide.

17. The method of claim 2 wherein the step of desulfurizing the product of step (b) comprises heating the product obtained from step (b) at a temperature sufficient to remove the $SR^1$ group.

18. The method of claim 2 wherein the aqueous alcohol solution contains sodium hydroxide, potassium hydroxide or barium hydroxide.

19. A method of preparing an α-aromatic propionic acid of the formula

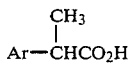

wherein Ar is an aromatic group selected from the group consisting of 4-alkylphenyl, 4-phenylphenyl, 4-alkoxyphenyl, 4-hydroxyphenyl, 2-hydroxyphenyl, 2,4-dihydroxyphenyl, 4-disubstituted aminophenyl, wherein each of said phenyl groups may be substituted by a substituent selected from the group consisting of alkyl, alkoxyl, hydroxy, disubstituted amino, halogen; naphythyl, 6-methoxy-naphth-2-yl, 2-methyoxy-naphth-1-yl, 2-thienyl, 3-indolyl and N-alkyprrolyl, comprising (a) reacting a compound of the formula

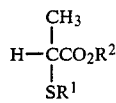

wherein $R^1$ is selected from the group consisting of an alkyl group, a phenyl group and a benzothiazolyl group, and $R^2$ is an alkyl group, with a chlorinating agent selected from sulfuryl choride and chlorine in an amount of from 1 to 5 chemical equivalents in the presence of a non-polar solvent, selected from carbon tetrachloride, methylene chloride, chloroform, benzene and toluene at a temperature of from −10° to 30° C. to produce an α-chlorinated product;

(b) reacting said α-chlorinated product with a compound having the formula ArH, wherein Ar is as defined above, in the presence of a Lewis acid selected from stannic chloride, titanium tetrachloride, zinc bromide, ferric chloride, aluminum chloride and zinc chloride in an amount of from 0.05 to 5 chemical equivalents and a non-reactive solvent selected from carbon tetrachloride, methylene chloride, carbon disulfide, nitromethane and nitrobenzene at a temperature of from −10° to 50° C. to produce a compound having the formula

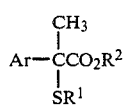

wherein Ar, $R^1$ and $R^2$ are as defined above;

(c) desulfurizing the product of step (b) to form a desulfurized product; and (d) hydrolyzing the desulfurized product in the presence of an aqueous solution or an aqueous alcohol solution.

20. The method of claim 19 wherein the Ar group is selected from 6-methoxy-naphth-2-yl, 4-methoxyphenyl and 4-hydroxyphenyl.

21. The method of claim 19 further comprising desulfurizing the product of step (b) in the presence of activated nickel.

22. The method of claim 19 further comprising desulfurizing the product of step (b) in the presence of (a) zinc and acetic acid or (b) sodium-t-butyl alcohol.

23. The method of claim 19 further comprising desulfurizing the product of step (b) in the presence of a reducing agent having an affinity for sulfur.

24. The method of claim 23 wherein the reducing agent is sodium methylmercaptide.

25. The method of claim 19 wherein the step of desulfuriizing the product of step (b) comprises heating the product obtained from step (b) at a temperature sufficient to remove the $SR^1$ group.

26. The method of claim 19 wherein the aqueous alcohol solution contains sodium hydroxide, potassium hydroxide or barium hydroxide.

* * * * *